United States Patent [19]

Leppard

[11] 4,430,425
[45] Feb. 7, 1984

[54] COLOR PHOTOGRAPHIC MATERIALS CONTAINING STABILIZERS

[75] Inventor: David G. Leppard, Rheinfelden, Switzerland

[73] Assignee: Ciba-Geigy AG, Basel, Switzerland

[21] Appl. No.: 389,995

[22] Filed: Jun. 18, 1982

[30] Foreign Application Priority Data

Jun. 19, 1981 [GB] United Kingdom ............... 8119014

[51] Int. Cl.³ .................... G03C 7/26; G03C 7/38
[52] U.S. Cl. ................................ 430/551; 430/372; 430/554; 430/562
[58] Field of Search ............. 430/551, 372, 554, 555, 430/562

[56] References Cited

U.S. PATENT DOCUMENTS

| | | | |
|---|---|---|---|
| 3,960,570 | 6/1976 | Oishi et al. | 430/551 |
| 4,232,114 | 11/1980 | Adachi et al. | 430/551 |
| 4,237,217 | 12/1980 | Arai et al. | 430/555 |
| 4,254,216 | 3/1981 | Uchida et al. | 430/372 |
| 4,277,558 | 7/1981 | Kikuchi et al. | 430/551 |
| 4,346,165 | 8/1982 | Sawada et al. | 430/551 |

*Primary Examiner*—J. Travis Brown
*Attorney, Agent, or Firm*—Joseph G. Kolodny

[57] ABSTRACT

Color photographic silver halide material which contains in at least one coupler containing silver halide emulsion layer or in a layer adjacent thereto
(a) a hydroquinone of the formula

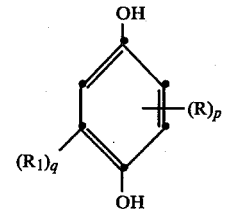

wherein p is 1 or 2 and q is 0 or 1, provided that p+q is 1 or 2, R is a radical of the formula

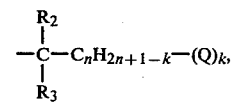

wherein Q is selected from the residues
(1) $-COZR_4$, wherein Z is O or $NR_5$, and $R_4$ is hydrogen, alkyl optionally interrupted by oxygen, cycloalkyl, alkenyl, aryl, aralkyl or a heterocyclic ring, and $R_5$ is hydrogen or alkyl or together with $R_4$ and the nitrogen atom to which they are bonded form a heterocyclic ring,
(2) $-OX$, wherein X is $R_5$ or $-COR_7$ is hydrogen, alkyl cycloalkyl, alkenyl, aryl or aralkyl,
(3) $-NR_8R_9$, wherein $R_8$ is hydrogen or alkyl, and $R_9$ is hydrogen, alkyl or $-COR_7$, or $R_8$ and $R_9$ together with the nitrogen atom to which they are bonded form a ring,
(4) $-P(O)(OR_{10}')([O]_xR_{11}')$, wherein x is 0 or 1, and if x is 1, $R_{10}'$ and $R_{11}'$ are hydrogen or alkyl or form together an alkylene chain, and if x is 0 $R_{10}'$ is alkyl,
(5) $-SO_2NR_5R_6$, wherein $R_5$ and $R_6$ are hydrogen or alkyl, or
(6) cyano,
n is 1 to 20, k is 1 or 2, $R_2$ and $R_3$ are alkyl and if Q is $CO_2R_4$, either $R_2$ or $R_3$ is optionally substituted by $-CO_2R_4$, or $R_2$ and $R_3$ form together an alkylene chain, and $R_1$ is alkyl or a group of the formula

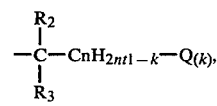

or
(b) a salt thereof, has an improved stability to light.

21 Claims, No Drawings

COLOR PHOTOGRAPHIC MATERIALS CONTAINING STABILIZERS

The present invention relates to colour photographic silver halide material containing hydroquinone compounds as stabilisers.

The chromogenous formation of colour photographic images is based on a substractive colour process wherein cyan, magenta and yellow images are formed by coupling reaction of a dye-forming coupler with the oxidation product of a developer compound which is in general an aromatic primary amine compound.

These colour images, however, are in general not sufficiently stable to light. The original colour density is reduced when colour images are exposed to light for a longer period. This means that the colour rendition is significantly impaired.

It is known from U.S. Pat. Nos. 3,432,300 and 3,573,050 to stabilize photographic colour images by incorporating derivatives of 5- or 6-hydroxychromane into colloid layers of a photographic, material which contain the colour coupler. It is further known from U.S. Pat. No. 3,930,866 to stabilize the magenta image using a combination of a phenol derivative and a pyrazolone magenta coupler in one silver halide emulsion layer of the photographic material. According to German Offenlegungsschrift No. 2.952.548 the same effect can be achieved by means of combination of an esterified hydroquinone compound with a pyrazolone coupler.

These photographic materials do not yet meet all current requirements with respect to the stability to light of the image dyestuffs.

It has now been found that the stability to light of colour photographic materials can be further improved by using certain substituted hydroquinone compounds as light stabilizers. These hydroquinone compounds further suppress the oxidation of the couplers during their addition to the photographic emulsions in the production of colour photographic materials.

Therefore, it is an object of the present invention to provide colour photographic materials which comprise improved light stabilizers.

Accordingly, there is provided a colour photographic silver halide material which comprises on a support at least one colour coupler containing silver halide emulsion layer, there being present in the silver halide emulsion layer(s) or in a layer adjacent to the silver halide emulsion layer(s)

(a) a hydroquinone compound of the formula

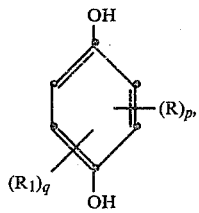

(1)

wherein p is 1 or 2 and q is 0 or 1, provided that p+q is 1 or 2, R is a radical of the formula

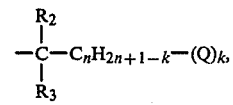

wherein Q is selected from the residues (1) —COZR$_4$, wherein Z is O or NR$_5$, and R$_4$ is hydrogen, alkyl having 1 to 20 carbon atoms, optionally interrupted by 1 to 5 oxygen atoms, and optionally substituted by a group OR$_6$, wherein R$_6$ is alkyl having 1 to 12 carbon atoms, cycloalkyl having 3 to 12 carbon atoms, alkenyl having 3 to 20 carbon atoms, aryl having 6 to 10 carbon atoms optionally substituted by one or two alkyl groups (each) having 1 to 4 carbon atoms or aralkyl having 7 to 13 carbon atoms or R$_4$ is alkenyl having 3 to 20 carbon atoms or cycloalkyl having from 3 to 12 carbon atoms, aryl having from 6 to 10 carbon atoms optionally substituted by alkyl having 1 to 4 carbon atoms, or aralkyl having from 7 to 13 carbon atoms, a 5 or 6 membered heterocyclic ring containing an oxygen atom, and optionally substituted by one or two alkyl groups (each) having 1 to 4 carbon atoms, or methyl substituted by a 5- or 6-membered heterocyclic ring containing an oxygen atom and optionally substituted by one or two alkyl groups (each) having 1 to 4 carbon atoms, and when Z is —NR$_5$, R$_5$ is hydrogen or alkyl having 1 to 20 carbon atoms, or R$_4$ and R$_5$ together with the nitrogen atom to which they are bonded form a 5 or 6 membered heterocyclic ring, optionally substituted by one or two alkyl groups (each) having 1 to 4 carbon atoms;

(2) —OX, wherein X is R$_5$ or COR$_7$, wherein R$_5$ is as defined above and R$_7$ is hydrogen or alkyl having 1 to 20 carbon atoms, alkenyl having 3 to 20 carbon atoms, cycloalkyl having 3 to 12 carbon atoms, aralkyl having 7 to 13 carbon atoms or aryl having 6 to 10 carbon atoms, optionally substituted by one or two alkyl groups each having 1 to 4 carbon atoms;

(3) —NR$_8$R$_9$ wherein R$_8$ is hydrogen or alkyl having 1 to 12 carbon atoms and R$_9$ is hydrogen, alkyl having 1 to 12 carbon atoms or —COR$_7$, wherein R$_7$ is as defined above, or R$_8$ and R$_9$, together with the nitrogen atom to which they are bonded, form a 5- or 6-membered ring, optionally substituted by one or two alkyl groups (each) having 1 to 4 carbon atoms;

(4) —P(O)(OR$_{10}'$)([O]$_x$R$_{11}'$) wherein x is 0 or 1, and if x is 1, R$_{10}'$ and R$_{11}'$ are independently of each other hydrogen or alkyl having 1 to 20 carbon atoms or R$_{10}'$ and R$_{11}'$ are linked together to form an alkylene chain having 2 or 3 carbon atoms optionally substituted by one or more alkyl groups each having 1 to 20 carbon atoms, and if x is 0, R$_{10}'$ is alkyl having 1 to 5 carbon atoms;

(5) —SO$_2$NR$_5$R$_7$, wherein R$_5$ and R$_7$ are as defined above, or (6) cyano;

n is an integer from 1 to 20, k is 1 or 2,

R$_2$ and R$_3$ are independently of each other alkyl having 1 to 5 carbon atoms and, if Q is CO$_2$R$_4$, either R$_2$ or R$_3$ is optionally substituted by —CO$_2$R$_4$, or R$_2$ or R$_3$ is so linked to the residue C$_n$H$_{2n+1-k}$ that there is formed a cycloalkylene residue having 5 to 12 carbon atoms substituted by —(CO$_2$R$_4$)$_k$, wherein R$_4$ and k are as defined above, R$_1$ is alkyl having 1 to 8 carbon atoms, or a residue of formula

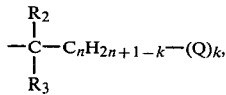

and if R$_1$ is a residue of this formula, then R$_1$ and R are the same or different; or (b) there being present salts thereof with organic or inorganic acids or bases.

A further object of the present invention is to provide a method for the preparation of the inventive photographic material.

Another object is the silver halide material produced by this method.

A further object is the use of the hydroquinone compounds of the formula (1) as light stabilizers in colour photographic material. R in the radicals of the formula (1) is a group of the formula

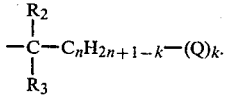

In this group, Q is a radical of the formula —COZR$_4$, wherein R$_4$ is hydrogen or alkyl having 1 to 20 carbon atoms. The alkyl groups R$_4$ can be straight or branched. Suitable alkyl groups are for example, methyl, ethyl, n-propyl, i-propyl, n-butyl, n-pentyl, i-pentyl, n-hexyl, n-heptyl, n-octyl, 2-ethylhexyl, n-nonyl, t-nonyl, n-decyl, n-dodecyl, n-tetradecyl, n-hexadecyl, n-octadecyl, or n-eicosyl. Those radicals having 1 to 16 carbon atoms are preferred. The alkyl radicals R$_4$ are optionally interrupted by 1 to 5, especially by 1, 2 or 3, oxygen atoms. Examples are radicals of the formulae —(C$_2$H$_4$O)$_3$—CH$_3$, —(C$_2$H$_4$O)$_2$—CH$_3$, —(C$_2$H$_4$O)$_3$—C$_2$H$_5$, —(C$_2$H$_4$O)$_2$—C$_2$H$_5$, or preferably radicals which are interrupted by 1 oxygen atom such as —C$_2$H$_4$—OCH$_3$, —C$_2$H$_4$—OC$_4$H$_9$, —C$_2$H$_4$—OC$_8$H$_{17}$-n or —C$_4$H$_8$—O—C$_{10}$H$_{21}$-n.

The straight or branched alkyl groups R$_4$ are optionally substituted by a group —OR$_6$. R$_6$ is alkyl having 1 to 12 carbon atoms. Suitable alkyl groups are those listed above for R$_4$. R$_6$ denotes further cycloalkyl radicals having 3 to 12 carbon atoms, for example, cyclopropyl, cyclobutyl, cyclopentyl, cyclohexyl, cyclooctyl, cyclodecyl, adamantyl or cyclododecyl, The preferred cycloalkyl radicals are cyclopentyl, cyclohexyl and cyclooctyl. Especially suitable are cyclopentyl and cyclohexyl. R$_6$ is further alkenyl having 3 to 20 carbon atoms. These alkenyl radicals can be straight or branched. Examples are prop-2-enyl, n-but-2-enyl, 2-methyl-prop-2-enyl, n-pent-2-enyl, n-hex-2-enyl, n-hexa-2,4-dienyl, n-dec-10-enyl or n-eicos-2-enyl. Preferred alkenyl radicals contain 3 to 10 carbon atoms and are e.g., prop-2-enyl, n-but-2-enyl and n-dec-10-enyl. R$_6$ denotes further aryl having 6 to 10 carbon atoms. The groups phenyl and naphthyl are preferred. Phenyl is a very suitable group. The aryl groups R$_6$ are optionally substituted by 1 or 2 alkyl groups (each) having 1 to 4 carbon atoms such as methyl, ethyl, n-propyl, i-propyl, n-butyl or t-butyl. Suitable alkyl substituted aryl groups R$_6$ are e.g. tolyl, xylyl, cumyl or butylphenyl. In the meaning of aralkyl having 7 to 13 carbon atoms, R$_6$ represents residues such as benzyl, phenylethyl, benzhydryl or naphthylmethyl. Benzyl and phenylethyl are preferred.

A further meaning for R$_4$ is alkenyl having 3 to 20 carbon atoms. Suitable examples of alkenyl groups for R$_4$ are those listed above for the definition of R$_6$. Alkenyl radicals having 3 to 15 carbon atoms are especially preferred. R$_4$ further denotes aryl having 6 to 10 carbon atoms. Suitable groups for R$_4$ are, e.g., phenyl or naphthyl, especially phenyl, optionally substituted by 1 or 2 alkyl groups (each) having 1 to 4 carbon atoms such as methyl, ethyl, n-propyl or n-butyl. Further, R$_4$ represents cycloalkyl having 3 to 12 carbon atoms. Suitable cycloalkyl groups R$_6$ are those listed above in the definition of R$_6$. Cyclooctyl and, more suitably, cyclopentyl and cyclohexyl are preferred. As aralkyl having 7 to 13 carbon atoms, R$_4$ denotes those radicals listed above in the definition of R$_6$. Phenylethyl and, especially, benzyl are preferred aralkyl radicals R$_4$. In a further meaning, R$_4$ is a 5 or 6 membered heterocyclic ring containing an oxygen atom. Examples are tetrahydrofuran-3-yl, tetrahydropyran-4-yl and 2,6-dimethyl-tetrahydropyran-4-yl. Tetrahydrofuran-3-yl is especially preferred. Optionally the heterocyclic rings R$_4$ are substituted by 1 or 2 alkyl groups (each) having 1 to 4 carbon atoms such as methyl, ethyl, i-propyl, n-butyl or t-butyl. In a further meaning, R$_4$ is methyl substituted by a 5 or 6 membered heterocyclic ring containing an oxygen atom which ring is optionally substituted by 1 or 2 alkyl groups (each) having 1 to 4 carbon atoms. An example of such ring system is tetrahydrofurfuryl or furfuryl. Z is O or NR$_5$.

R$_5$ is hydrogen or alkyl having 1 to 20 carbon atoms. Suitable examples of alkyl groups are those listed above for the definition of R$_4$. R$_5$ together with R$_4$ and the nitrogen atom to which they are bonded may form a 5 or 6 membered heterocyclic ring such as pyrrolidinyl, piperidinyl, pyrrolyl, pyridinyl or pyrazinyl. Pyrrolidinyl and piperidinyl are preferred. The heterocyclic rings R$_5$ are optionally substituted by 1 or 2 alkyl groups (each) having 1 to 4 carbon atoms.

Further, Q in the compounds of the formula (1) denotes a radical of the formula —OX, wherein X is R$_5$ or COR$_7$. R$_5$ is as defined above in connection with the substituent Z. R$_7$ is hydrogen or alkyl having 1 to 20 carbon atoms. Suitable alkyl groups R$_7$ are the same as cited above in the definitions of R$_4$. Those alkyl radicals R$_7$ are preferred which contain 1 to 10 carbon atoms. R$_7$ further denotes cycloalkyl, aryl and aralkyl. Suitable cycloalkyl and aralkyl groups are the same as cited above in the definitions of R$_6$. Aryl radicals which are suitable as R$_7$ are listed above in the definition of R$_4$.

Q further denotes a radical of the formula —NR$_8$R$_9$. R$_8$ is hydrogen or alkyl having 1 to 12 carbon atoms, such as methyl, ethyl, n-propyl, i-propyl, n-butyl, t-butyl, n-pentyl or i-pentyl. Further suitable alkyl radicals are listed above for R$_4$. R$_9$ has the same meaning as R$_8$ and denotes further COR$_7$, wherein R$_7$ is as defined above in connection with the radical X. R$_8$ and R$_9$ also form together with the nitrogen atom to which they are bonded a ring system, preferably a 5 or 6 membered ring, such as pyrrolidine, piperidine, morpholine or 2,5-dimethylmorpholine. These ring systems are optionally substituted by alkyl groups, preferably 1 or 2 alkyl groups, which contain 1 to 4 carbon atoms such as methyl, ethyl, n-propyl, i-propyl, n-butyl, t-butyl, or i-pentyl.

Q is further a radical of the formula —P(O)(OR$_{10}'$)-([O]$_x$R$_{11}'$), wherein X is 0 or 1. If x is 1, then R$_{10}'$ and R$_{11}'$ are independently of each other hydrogen or alkyl having 1 to 20 carbon atoms. Suitable alkyl radicals are those which are cited in the definitions of R$_4$. R$_{10}'$ and R$_{11}'$ also form together an alkylene chain which preferably contains 2 or 3 carbon atoms and is optionally substituted by one or more alkyl groups (each) having 1 to 20 carbon atoms, which are defined above. If X is 0, R$_{10}'$ is alkyl, preferably having 1 to 5 carbon atoms, such as methyl, ethyl, n-propyl, n-butyl, t-butyl or i-pentyl.

Further, Q denotes a radical of the formula —SO$_2$NR$_5$R$_7$, wherein R$_5$ and R$_7$ are as defined above. Q denotes further cyano.

Preferably, in the compounds of the formula (1), p and q each are 1 and the substituent R is in meta-position or preferably, in para-position to R$_1$.

Index k denotes 1 or 2, preferably 1, and n is an integer from 1 to 20. More suitable are those radicals of the formula (1), wherein n is an integer from 1 to 10 or especially, from 1 to 6. Most preferably, n denotes an integer from 1 to 3.

R$_2$ and R$_3$ are, independently of each other, alkyl each having 1 to 5 carbon atoms. Examples are methyl, ethyl, n-propyl, i-propyl, n-butyl, s-butyl, n-pentyl or neopentyl. Preferably, R$_2$ and R$_3$ are independently of each other methyl, ethyl or neopentyl. The alkyl groups R$_2$ and R$_3$ are optionally substituted by —COZR$_4$, wherein Z and R$_4$ are as defined above. However, if R$_2$ is substituted by —COZR$_4$ then R$_3$ is unsubstituted, and if R$_3$ is substituted by —COZR$_4$ then R$_2$ is unsubstituted. Further, R$_2$ or R$_3$ may be so linked with the residue C$_n$H$_{2n+1-k}$ that there is formed a cycloalkylene radical having 5 to 12 carbon atoms. Cycloalkylene radicals having 5 to 8 carbon atoms are preferred. The cycloalkylene radicals formed by R$_2$ or R$_3$ are optionally substituted by 1 or 2 groups —COZR$_4$, wherein Z and R$_4$ are as defined above.

R$_1$ is a group of the formula

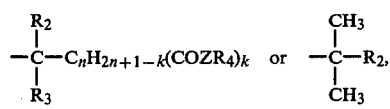

wherein R$_2$, R$_3$, R$_4$, Z, k and n have the meanings assigned to them above. Preferably, in these formulae k is 1.

The hydrouqinone compounds of the formula (1) can further be present in salt form. These salts are produced by reaction of a compound of the formula (1) with organic or inorganic bases. Bases which can be used, are for example, alkali or alkaline earth hydroxides or carbonates such as NaOH, KOH, Mg(OH)$_2$, Ca(OH)$_2$ or Na$_2$CO$_3$, as well as tetra-alkyl ammonium hydroxides such as (CH$_3$)$_4$N(OH) or (C$_2$H$_5$)$_4$N(OH) or guanidine.

The colour couplers which can be present in the inventive material together with the hydroquinone compound of the formula (1) are preferably magenta couplers e.g. those described in U.S. Pat. Nos. 2,311,081, 3,127,269, 3,658,544 and GB Pat. No. 956,261. Suitable magenta couplers have the formulae

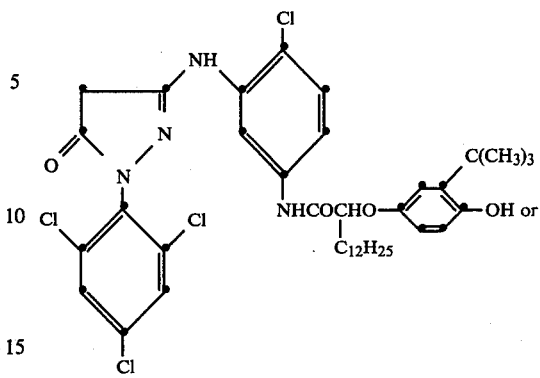

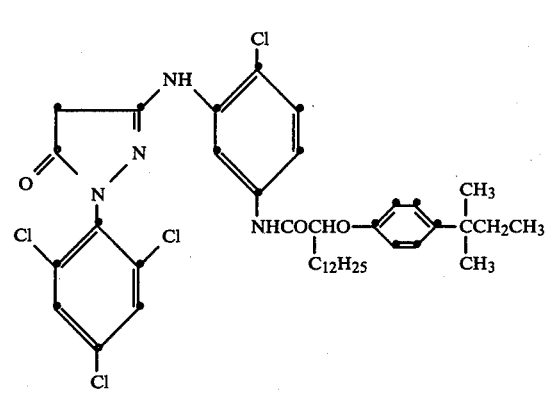

A suitable photographic material contains a hydroquinone compound of the formula

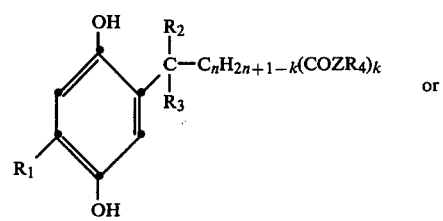

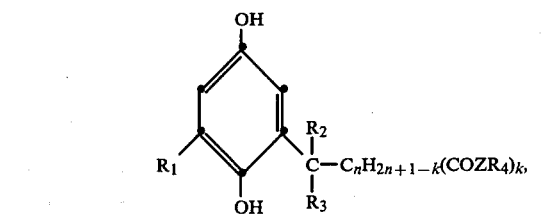

wherein k, Z, R$_1$, R$_2$ R$_3$, R$_4$ and n are as defined above or a hydroquinone compound of the formula

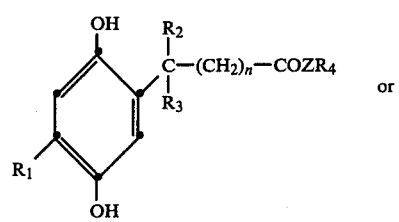

-continued

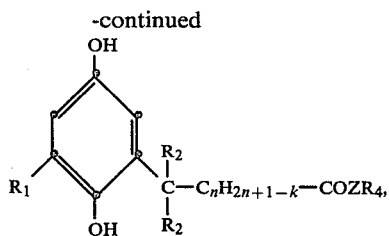

wherein
R₄, Z and n are as defined above,
R₂ and R₃ independently of each other, are alkyl each having 1 to 5 carbon atoms and either R₂ or R₃ is optionally substituted by —COZR₄, wherein Z and R₄ are as defined above, or R₂ or R₃ may be so linked with the residue $C_nH_{2n}$ that there is formed a cycloalkylene residue having 5 to 12 carbon atoms which is substituted by —COZR₄, wherein Z and R₄ are as defined above, and
R₁ is a group of the formulae

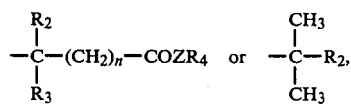

wherein R₂, R₃, R₄, Z and n are as defined above, or salts thereof with organic or inorganic acids or bases.

Preferably, a photographic material is used wherein the hydroquinone compound has the formula

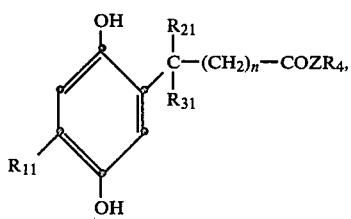

wherein
R₂₁ and R₃₁, independently of each other, are methyl, ethyl, n-propyl, i-propyl or neopentyl and either R₂₁ or R₃₁ is optionally substituted by —COZR₄, wherein Z and R₄ are as defined above, or
R₂₁ or R₃₁ may be so linked with the residue $C_nH_{2n}$ that there is formed a cycloalkylene residue having 5 to 8 carbon atoms which is optionally substituted by —COZR₄, wherein Z and R₄ are as defined above, R₁₁ is a group of the formula:

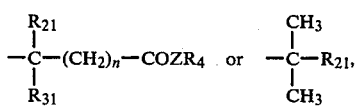

wherein R₂₁, R₃₁, Z, R₄ and n are as defined above, or a salt thereof with organic or inorganic acids or bases.

In a valuable photographic material they hydroquinone compound corresponds to the formula

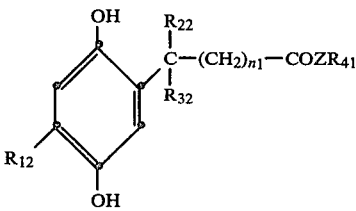

wherein
Z is O or NR₅
R₄₁ is hydrogen, alkyl having from 1 to 20 carbon atoms optionally interrupted by 1, 2 or 3 oxygen atoms and optionally substituted by —OR₆₁, wherein R₆₁ is cyclopentyl, cyclohexyl or cyclooctyl, alkenyl having 3 to 10 carbon atoms, phenyl or naphthyl optionally substituted by 1 or 2 alkyl groups (each) having 1 to 4 carbon atoms, benzyl, phenylethyl, benzhydryl or naphthylmethyl, or R₄₁ is alkenyl having 3 to 15 carbon atoms, phenyl or naphthyl optionally substituted by 1 or 2 alkyl groups (each) having 1 to 4 carbon atoms, cyclopentyl, cyclohexyl, cyclooctyl, benzyl, phenylethyl, benzhydryl or naphthylmethyl, or R₄₁ is a 5 or 6 membered heterocyclic ring containing an oxygen atom which ring is optionally substituted by 1 or 2 alkyl groups (each) having 1 to 4 carbon atoms or R₄₁ is methyl substituted by a 5 or 6 membered heterocyclic ring containing an oxygen atom which ring is optionally substituted by 1 or 2 alkyl groups (each) having 1 to 4 carbon atoms,
R₂₂ and R₂₃, independently of each other, are methyl, ethyl or neopentyl or may be so linked to the residue $(CH_2)_{n1}$ that there is formed a cyclohexylene residue, which is optionally substituted by —COZR₄ wherein R₄ and Z have their previous significance,
R₁₂ is a group of the formulae

wherein R₂₂, R₃₂ and R₄₁ are as defined above and n₁ is an integer from 1 to 10,
or to salts thereof with organic or inorganic acids or bases.

A useful photographic material contains a hydroquinone compound of the formula

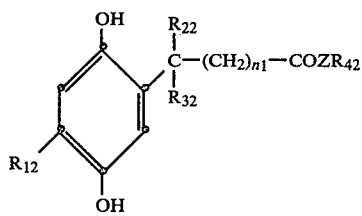

wherein
Z is O or NR₅₁
R₄₂ is alkyl having from 1 to 20 carbon atoms optionally interrupted by 1 or 2 oxygen atoms and optionally substituted by —OR₆₂, wherein R₆₂ is cyclohexyl, alkenyl having 3 to 10 carbon atoms, phenyl
or benzyl, or $R_{42}$ is alkenyl having 3 to 15 carbon
atoms, phenyl, benzyl, phenylethyl, cyclopentyl or
cyclohexyl or $R_{42}$ is a 5 or 6 membered heterocyclic ring containing an oxygen atom or $R_{42}$ is
methyl substituted by a 5 or 6 membered heterocyclic ring containing an oxygen atom, $R_{51}$ is hydrogen or alkyl having 1 to 15 carbon atoms, and $R_{12}$, $R_{22}$, $R_{32}$ and $n_1$ are as defined above, or salts thereof with organic or inorganic bases or acids.

Interesting photographic material contains a hydroquinone compound of the formula

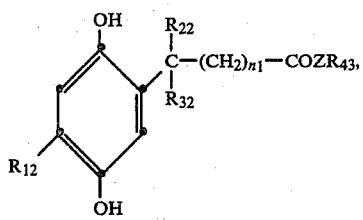

wherein $R_{43}$ is alkyl having 1 to 16 carbon atoms optionally interrupted by an oxygen atom and optionally substituted by phenoxy, or $R_{43}$ is alkenyl having 3 to 15 carbon atoms, phenyl, benzyl, tetrahydrofuran-3-yl, tetrahydropyran-4-yl or tetrahydrofufuryl and Z, $R_{12}$, $R_{22}$, $R_{32}$, $R_{51}$ and $n_1$ are as defined above, or there being present a salt produced by reaction of the compound of the formula (11) with organic or inorganic bases.

In a suitable photographic material a salt produced by reaction of the compounds of the formulae (1) to (11) with tetra-alkyl ammonium hydroxides or alkali or alkaline earth hydroxides or carbonates is present.

Especially suitable is a photographic material, wherein the hydroquinone compound corresponds to the formula

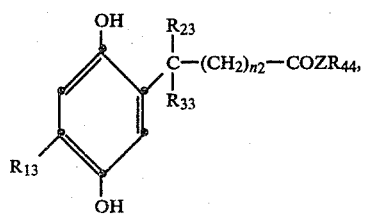

wherein
$R_{44}$ is alkyl having 1 to 16 carbon atoms optionally interrupted by an oxygen atom and optionally substituted by phenoxy, or $R_{44}$ is phenyl, benzyl, tetrahydrofuran-3-yl or tetrahydrofurfuryl, and Z and $R_{51}$ are as defined above,
$R_{23}$ and $R_{33}$, independently, are methyl or neopentyl,
$R_{13}$ is a group of the formula

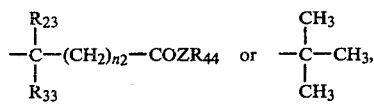

wherein $R_{23}$, $R_{33}$ and $R_{44}$ are as defined above, and $n_2$ is an integer from 1 to 3.

Further suitable materials contain the hydroquinone of the formula

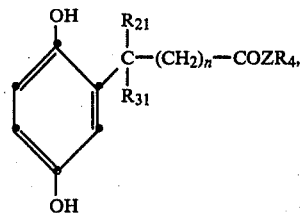

wherein $R_{21}$, $R_{31}$, $R_4$, Z and n are as defined above.

Further suitable materials contain a hydroquinone of the formula

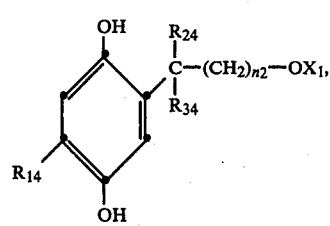

wherein
$X_1$ is $COR_7$, wherein $R_7$ is hydrogen or alkyl having 1 to 10 carbon atoms, or $X_1$ is hydrogen or alkyl having 1 to 10 carbon atoms,
$R_{24}$ and $R_{34}$ are independently of each other methyl or ethyl, and
$R_{14}$ is a group of the formula

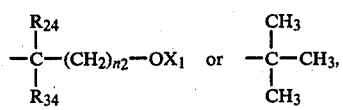

wherein $X_1$, $R_{24}$ and $R_4$ are as defined above and $n_3$ is an integer from 1 to 6.

Further suitable materials contain a hydroquinone of the formula

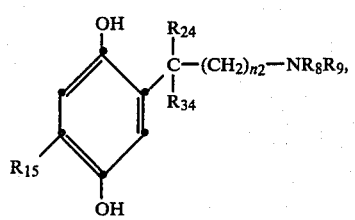

wherein
$R_8$ is hydrogen, methyl or ethyl, $R_9$ is hydrogen, methyl, ethyl or $COR_7$, wherein $R_7$ is as defined in claim 11,
$R_{15}$ is a group of the formula

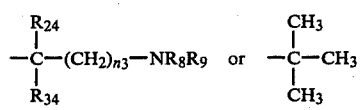

wherein $R_8$, $R_9$, $R_{24}$, $R_{34}$ and $n_2$ are as defined above.

Further suitable materials contain a hydroquinone of the formula

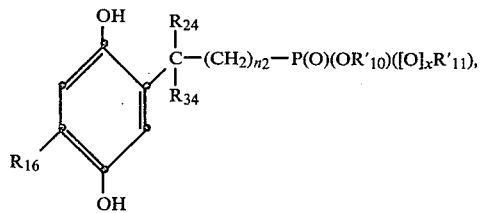

(16)

wherein

X is 1 or 0, $R_{10}'$ and $R_{11}'$ are independently of each other hydrogen or alkyl having 1 to 12 carbon atoms if x is 1, and are alkyl having 1 to 5 carbon atoms if x is 0, $R_{16}$ is a group of the formula

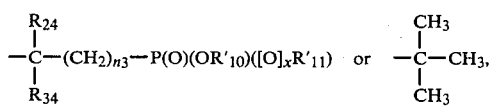

wherein x, $R_{10}'$, $R_{11}'$, $R_{24}$, $R_{34}$ and $n_2$ are as defined above.

Further suitable materials contain a hydroquinone of the formula

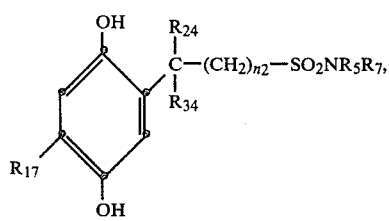

(17)

wherein $R_5$ and $R_7$ are hydrogen or alkyl having 1 to 10 carbon atoms, $R_{17}$ is a group of the formula

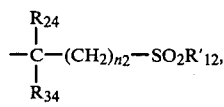

wherein $R_{12}'$, $R_{24}$, $R_{34}$ and $n_2$ are as defined above.

Further suitable materials contain a hydroquinone of the formula

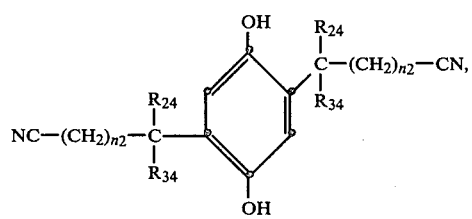

(18)

wherein $R_{24}$, $R_{34}$ and $n_3$ are as defined above.

Further suitable materials contain a hydroquinone of the formula

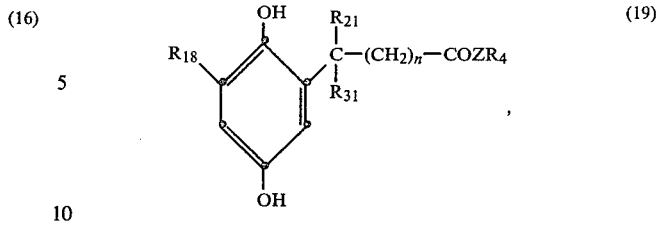

(19)

wherein $R_{21}$, $R_{22}$, $R_4$, Z and n are as defined above and $R_{18}$ is a radical of the formula

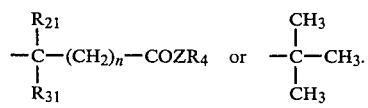

A very useful photographic material contains a combination of a hydroquinone compound according to the formula (1) and a magenta coupler. The magenta coupler has preferably the formula

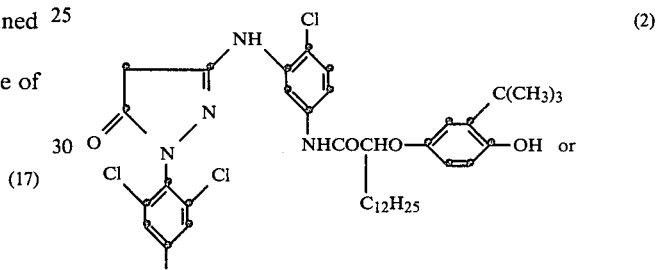

(2)

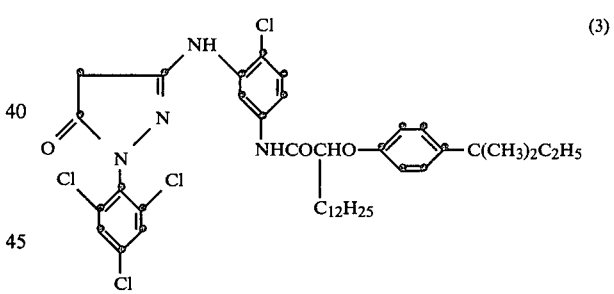

(3)

The inventively used hydroquinone compounds are prepared by reacting a hydroquinone with a functional alkylating agent capable of introducing an optionally substituted alkyl residue into the hydroquinone in the presence of a catalyst and at higher temperatures. The alkylating agent contains a reactive centre, e.g. an olefinic or hydroxyl group. The alkylation step is conveniently carried out at a temperature ranging from 20° C. to 150° C., but preferably in the range 80°–130° C. The acid catalyst may be a Bronsted or Lewis acid or active earth. Bronsted acids suitable for the purpose may be organic or inorganic or a partial salt thereof and may be an inorganic mineral acid such as hydrochloric, sulphuric, perchloric, and orthophosphoric acid; an alkyl, aryl or alkaryl substituted inorganic acid such as methane and ethane sulphonic acids, benzene sulphonic acid p-toluene sulphonic acid and methane phosphonic acid; an organic acid such as dichloro acetic acid, trichloroacetic acid, and trifluoroacetic acids. Lewis acids suitable for alkylation include boron trifluoride, ferric chloride, aluminium chloride, and stannic chloride. Active earths suitable for alkylation include Fulmont 237 (trademark) and Fulcat 22 (trademark). The preferred catalyst for the alkylation is p-toluene sulphonic acid.

The hydroquinone compounds of the formula (1) as well as the colour couplers can be incorporated in a known manner in photographic layers, for example in silver halide emulsions containing gelatine and/or other binders. The hydroquinone compounds are further suitable for use in silver dye-bleach materials.

For example, they can be used in silver bromide, silver chloride or silver iodide emulsions or in those emulsions which contain a mixture of silver halides, such as silver bromide/iodide or silver chloride/bromide emulsions, or in a layer adjacent thereto.

The emulsions can be chemically sensitised and they can also contain customary organic stabilisers and antifogging agents as well as customary plasticisers, for example glycerine. The emulsions can also be hardened with the hardeners customary for gelatine. Furthermore, the emulsions can contain customary coating assistants. The emulsions can be applied to layer supports customary for photographic recording material. Optionally, a mixture of several colloids can be used to disperse the silver halides.

The customary developer baths can be employed for developing the recording material for colour photography. These baths as a rule contain a developer substance of the p-phenylenediamine type, a development retarder, such as potassium bromide, an antioxidant, such as sodium sulfite, and a base, for example an alkali metal hydroxide or alkali metal carbonate. Furthermore, the developer baths can contain a conventional antifogging agent and complexing agents.

Corresponding application possibilities are described, for example, in U.S. Pat. Nos. 2,304,939, 2,304,940, 2,322,027, 2,284,879, 2,801,170, 2,801,171, 2,749,360 and 2,825,382.

The following Examples further illustrate the present invention. Parts and percentages shown therein are by weight.

EXAMPLE 1

110 Parts of hydroquinone, 284 parts of methyl 5-methylhex-5-enoate, and 10 parts of p-toluene sulphonic acid are heated on a steambath for 24 hours. The cooled reaction mixture partially solidified and after trituration with either, yields after filtration, 2,5-bis-(5-methoxycarbonyl-2-methylpent-2-yl)-hydroquinone [formula (101)] m.p. 150°-153° C. After crystallisation from methanol water, the product has a m.p. of 160°-162° C. with the following percentage composition by weight:

|  | Carbon | Hydrogen |
|---|---|---|
| Found | 67.05 | 8.96 |
| Calculated for $C_{22}H_{34}O_6$ | 66.98 | 8.69 |

EXAMPLE 2

25.0 Parts of 2,5-bis-(5-methoxycarbonyl-2-methylpent-2-yl)-hydroquinone, 250 parts of glacial acetic acid, and 125 parts of 46% aqueous hydrobromic acid are stored for 15 hours at room temperature. At the end of this period 2,5-bis-(5-carboxy-2-methyl-pent-2-yl)-hydroquinone [formula (102)] containing 1 molecule of acetic acid of crystallisation, is filtered off with a m.p. 221°-224° C. and with the following percentage composition by weight:

|  | Carbon | Hydrogen |
|---|---|---|
| Found | 63.68 | 8.38 |
| Calculated for $C_{20}H_{30}O_6 \cdot CH_3CO_2H$ | 63.30 | 8.60 |

5.0 Parts of 2,5-bis-(5-carboxy-2-methylpent-2-yl)-hydroquinone, 100 parts of absolute ethanol, and 1.0 parts of 98% sulphuric acid are refluxed for 16 hours. The solution is then stripped down under reduced pressure, the residue taken up in ether, and washed with sodium bicarbonate solution. The ethereal solution after being concentrated and diluted with 40°-60° petroleum ether yields 2,5-bis-(5-ethoxycarbonyl-2-methylpent-2-yl)-hydroquinone, [formula (103)] m.p. 146°-149° C. with the following percentage composition by weight:

|  | Carbon | Hydrogen |
|---|---|---|
| Found | 68.62 | 9.43 |
| Calculated for $C_{24}H_{38}O_6$ | 68.22 | 9.06 |

Compounds (104) to (122) in the following table further exemplify esters similarly prepared from 2,5-bis-(5-carboxy-2-methylpent-2-yl)-hydroquinone, according to the procedure described in Example 2.

TABLE 1

Hydroquinones of the formula

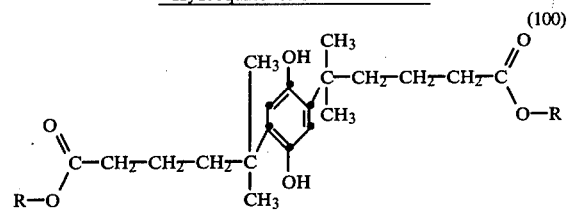

(100)

| Compound | R | m.p. °C. | Molecular Formula | Found and Required Composition (%) | |
|---|---|---|---|---|---|
|  |  |  |  | Carbon | Hydrogen |
| 104 | n-hexyl | 85–87 | $C_{32}H_{54}O_6$ | 71.77 | 10.23 |
|  |  |  |  | 71.87 | 10.18 |
| 105 | n-heptyl | 87–88 | $C_{34}H_{58}O_6$ | 72.75 | 10.48 |
|  |  |  |  | 72.56 | 10.39 |
| 106 | 2-ethylhexyl | 60–62 | $C_{36}H_{62}O_6$ | 73.15 | 10.76 |
|  |  |  |  | 73.18 | 10.58 |
| 107 | n-octyl | 77–80 | $C_{36}H_{62}O_6$ | 73.39 | 10.71 |
|  |  |  |  | 73.18 | 10.58 |
| 108 | n-hexadecyl | 81–84 | $C_{52}H_{94}O_6$ | 76.48 | 11.59 |
|  |  |  |  | 76.65 | 11.54 |
| 109 | tetrahydrofurfuryl | 112–114 | $C_{30}H_{46}O_8$ | 67.23 | 8.90 |
|  |  |  |  | 67.39 | 8.67 |
| 110 | 2-n-butoxyethyl | 87–89 | $C_{32}H_{54}O_8$ | 67.70 | 9.88 |
|  |  |  |  | 67.81 | 9.60 |
| 111 | 2-phenoxyethyl | 140–143 | $C_{36}H_{46}O_8$ | 70.63 | 7.98 |
|  |  |  |  | 71.26 | 7.64 |
| 112 | benzyl | 139–141 | $C_{34}H_{42}O_6$ | 74.57 | 7.89 |
|  |  |  |  | 74.70 | 7.74 |
| 113 | n-propyl | 134–136 | $C_{26}H_{42}O_6$ | 69.08 | 9.29 |
|  |  |  |  | 69.30 | 9.36 |
| 114 | i-propyl | 140–143 | $C_{26}H_{42}O_6$ | 68.57 | 9.70 |
|  |  |  |  | 69.30 | 9.36 |
| 115 | n-butyl | 105–108 | $C_{28}H_{46}O_6$ | 70.54 | 9.97 |
|  |  |  |  | 70.26 | 9.69 |
| 116 | i-butyl | 135–138 | $C_{28}H_{46}O_6$ | 70.57 | 9.97 |
|  |  |  |  | 70.26 | 9.96 |
| 117 | n-pentyl | 80–84 | $C_{30}H_{50}O_6$ | 71.88 | 11.10 |
|  |  |  |  | 71.11 | 9.95 |
| 118 | i-pentyl | 94–97 | $C_{30}H_{50}O_6$ | 70.65 | 9.97 |
|  |  |  |  | 71.11 | 9.95 |

TABLE 1-continued

Hydroquinones of the formula

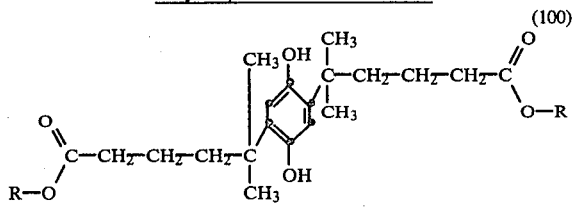
(100)

| Compound | R | m.p. °C. | Molecular Formula | Found and Required Composition (%) Carbon | Hydrogen |
|---|---|---|---|---|---|
| 119 | cyclohexyl | 176–180 | $C_{32}H_{50}O_6$ | 72.61 72.42 | 9.74 9.50 |
| 120 | n-dodecyl | 77–79 | $C_{44}H_{78}O_6$ | 75.46 75.21 | 10.91 11.11 |
| 121 | n-hexadecyl | 81–84 | $C_{52}H_{94}O_6$ | 76.48 76.65 | 11.59 11.54 |
| 122 | allyl | 136–139 | $C_{26}H_{38}O_6$ | 70.14 69.93 | 8.61 8.58 |

EXAMPLE 3

8.0 Parts of 2,5-bis-(5-methoxycarbonyl-2-methyl-pent-2-yl)-hydroquinone, 100 parts of furfuryl alcohol and 1.0 parts of sodium methoxide are heated on a steam-bath for 24 hours. The cooled reaction mixture is diluted with ether and washed with water. After removing the ether and excess furfuryl alcohol, the residue is triturated with 40°–60° petroleum ether containing ether to yield 2,5-bis-(5-furfuryloxycarbonyl-2-methyl-pent-2-yl)-hydroquinone, [formula (123)] m.p. 139°–142° C. Crystallisation from methanol containing 5% water yields crystals of m.p. 140°–143° C. with the following percentage composition by weight:

| | Carbon | Hydrogen |
|---|---|---|
| Found | 67.45 | 7.50 |
| Calculated for $C_{30}H_{38}O_8$ | 68.42 | 7.27 |

EXAMPLE 4

(a) 16.6 Parts of 2-t-butylhydroquinone, 14.2 parts of methyl 5-methyl-hex-5-enoate and 0.5 part of p.toluene sulphonic acid are heated on a steam-bath for 24 hours. The reaction mixture is then taken up in ether, washed with dilute sodium hydroxide solution, and then with water. After removing ether and lower boilers, distillation gave methyl 5-(4-t-butyl-2,5-dihydroxy-phenyl)-5-methyl-hexanoate, [formula (124)], $b_{0.3}$ 186°–210° C. This fraction after crystallisation from petroleum ether, had a m.p. 136°–139° C. and the following percentage composition by weight:

| | Carbon | Hydrogen |
|---|---|---|
| Found | 70.39 | 9.39 |
| Calculated for $C_{18}H_{28}O_4$ | 70.10 | 9.15 |

(b) 5 Parts of methyl 5-(4-t-butyl-2,5-dihydroxyphenyl)-5-methylhexanoate is converted to the corresponding n-hexyl ester after reaction with 20 parts n-hexanol and 0.25 part of sodium methoxide in a sealed glass tube for 7 days. The reaction mixture is diluted with ether, washed with dilute hydrochloric acid, then water, and stripped of ether and excess hexanol under reduced pressure to give a residue. Short-path distillation of the residue at 0.4 mb yields n-hexyl 5-(4-t-butyl-2,5-dihydroxyphenyl)-5-methyl-hexanoate [formula (125)] as an amber oil with the following percentage composition by weight:

| | Carbon | Hydrogen |
|---|---|---|
| Found | 72.33 | 10.26 |
| Calculated for $C_{23}H_{38}O_4$ | 72.98 | 10.12 |

EXAMPLE 5

Similarly by the procedure of Example 4(b) from n-decanol and the methyl ester of Example 4(a) is prepared n-dodecyl 5-(4-t-butyl-2,5-di-hydroxyphenyl)-5-hexanoate [formula (126)] with the following percentage composition by weight:

| | Carbon | Hydrogen |
|---|---|---|
| Found | 75.49 | 11.01 |
| Calculated for $C_{29}H_{50}O_4$ | 75.28 | 10.89 |

EXAMPLE 6

83 Parts of 4-t-butylhydroquinone, 19.8 parts of methyl 5,7,7-trimethyloct-4-enoate, and 5.0 parts of Fulmont 237 (trademark) are stirred at 130° C. for 24 hours. The reaction mixture is then diluted with ether, filtered, and evaporated to give a residue. A short-path rotary distillation of this residue at 0.13 mb yields, after removing lower boilers, methyl 5-(4-t-butyl-2,5-dihydroxyphenyl)-5,7,7-trimethyl-octanoate [formula (127)] with the following percentage composition by weight:

| | Carbon | Hydrogen |
|---|---|---|
| Found | 72.72 | 9.32 |
| Calculated for $C_{22}H_{36}O_4$ | 72.49 | 9.95 |

EXAMPLE 7

5.5 Parts of hydroquinone, 21.2 parts of n-hexyl 5-methylhex-5-enoate, and 1.0 parts of p-toluene sulphonic acid are heated on a steam-bath for 4 days. The cooled reaction mixture is taken up in ether, washed with 10% sodium hydroxide solution and then with water, until neutral. After stripping, the residual oil which partially solidified, is triturated with 40°–60° petroleum ether and gave 2,5-bis-(5-n-hexyloxycarbonyl-2-methyl-pent-2-yl)-hydroquinone [formula (128)] m.p. 77°–78° C. A further crystallisation from 60°–80° petroleum ether gives material m.p. 83°–86° C. identical with that obtained in Example 9.

EXAMPLE 8

2.0 Parts of bis-2,5-(5-methoxycarbonyl-2-methyl-pent-2-yl)-hydroquinone, and 15.0 parts of n-butylamine are refluxed for 18 hours and the excess butylamine then removed under reduced pressure. The residue after treatment with ether gives 2,5-bis-(5-N-n-butylcarbamoyl-2-methyl-pent-2-yl)-hydroquinone [formula (129)], which after crystallisation from ethanol, has m.p. 198°–200° C. and the following percentage composition by weight.

|  | Carbon | Hydrogen | Nitrogen |
|---|---|---|---|
| Found | 70.39 | 10.21 | 5.83 |
| Calculated for $C_{28}H_{48}N_2O_4$ | 70.55 | 10.15 | 5.88. |

EXAMPLE 9

2.0 Parts of bis-2,5-(5-methoxycarbonyl-2-methyl-pent-2-yl)-hydroquinone, and 10.0 parts of di-n-butylamine are sealed into a glass Carius tube and heated at 160° C. for 72 hours. After removing the excess dibutylamine under reduced pressure, the solid residue is washed with ether and gives bis-2,5-(5-di-N,N-n-butyl-carbamoyl-2-methyl-pent-2-yl)-hydroquinone [formula (130)], m.p. 175°–179° C. Two further crystallisations from ethanol gives product m.p. 190°–192° C. with the following percentage composition by weight.

|  | Carbon | Hydrogen | Nitrogen |
|---|---|---|---|
| Found | 73.06 | 11.35 | 4.83 |
| Calculated for $C_{36}H_{64}N_2O_4$ | 73.42 | 10.95 | 4.76. |

EXAMPLE 10

5.5 Parts of hydroquinone, 19.8 parts of citronnellyl acetate and 1.0 parts of p-toluene sulphonic acid are heated on a steambath for 24 hours. The reaction mixture is then taken up in ether, washed with 10% sodium hydroxide solution, water, and evaporated to give a residue. This residue is distilled using a short-path distillation at 0.13 mb and gives 2,5-bis-(8-acetoxy-2,6-dimethyl-oct-2-yl)-hydroquinone [formula (131)] as a viscous amber oil which slowly solidified.

Crystallisation from 60°–80° petroleum-ether gives product m.p. 60°–62° C. and the following percentage composition by weight.

|  | Carbon | Hydrogen |
|---|---|---|
| Found | 73.18 | 10.58 |
| Calculated for $C_{36}H_{62}O_6$ | 73.15 | 10.76. |

EXAMPLE 11

5.5 Parts of hydroquinone, 15.4 parts of 1-methyl-4-methoxycarbonyl-cyclohex-1-ene, and 0.5 parts of p-toluene sulphonic acid are heated on a steam-bath for 3 days. The reaction mixture after dilution with ether gives a stereoisomeric mixture of 2,5-bis-(4-methoxycarbonyl-1-methyl-cyclohex-1-yl)-hydroquinones [formula (132)] m.p. 266°–283° C. Crystallisation from dimethylformamide and water gives product m.p. 268°–287° C. containing 1 mole of dimethylformamide of crystallisation, and the following percentage composition by weight.

|  | Carbon | Hydrogen | Nitrogen |
|---|---|---|---|
| Found | 65.65 | 8.32 | 2.28 |
| Calculated for $C_{24}H_{34}O_6 \cdot C_3H_7NO$ | 65.96 | 8.41 | 2.85. |

EXAMPLE 12

12.4 Parts of toluhydroquinone, 21.2 parts of n-hexyl-5-methyl-hex-5-enoate, and 0.3 parts of p-toluene sulphonic acid are reacted and worked up as described in Example 25.

Distillation under reduced pressure gives a fraction $b_{0.1}$ 217°–226° C. which analysis showed to contain 14% of n-hexyl 5-(2,5-dihydroxy-3-methylphenyl)-5-methyl-hexanoate [formula (133a)] and 82% of n-hexyl-5-(2,5-dihydroxy-4-methylphenyl)-5-methyl-hexanoate [formula (133b)] and which has the following percentage composition by weight:

|  | Carbon | Hydrogen |
|---|---|---|
| Found | 71.24 | 10.11 |
| Calculated for $C_{20}H_{32}O_4$ | 71.39 | 9.59 |

EXAMPLE 13

The mother liquors from the preparation of 2,5-bis-(5-methoxy-carbonyl-2-methylpent-2-yl)-hydroquinone, in Example 1, are concentrated and then distilled. A fraction $b_{0.5}$ 160°–240° C. was collected and diluted with 40°–60° petroleum ether. From this solution there crystallises 2-(5-methoxycarbonyl-2-methylpent-2-yl)-hydroquinone [formula (134)], m.p. 102°–104° C. with the following percentage composition by weight.

|  | Carbon | Hydrogen |
|---|---|---|
| Found | 66.65 | 7.99 |
| Calculated for $C_{14}H_{20}O_4$ | 66.45 | 8.45. |

EXAMPLE 14

5.5 Parts of hydroquinone, 22,8 parts of 1,7-dimethoxycarbonyl-4-methylhept-3-ene and 1.0 parts of p-toluene sulphonic acid, are heated on a steam-bath for 3 days. After dilution with ether the reaction mixture is washed with sodium bicarbonate solution, water, evaporated and distilled to give dimethyl 5-methyl-5-(2,5-dihydroxyphenyl)-azelate, [formula (135)], $b_{0.1}$ 260°–269° C. with the following percentage composition by weight.

|  | Carbon | Hydrogen |
|---|---|---|
| Found | 64.34 | 7.92 |
| Calculated for $C_{18}H_{26}O_6$ | 63.89 | 7.74. |

EXAMPLE 15

41.4 Parts of 2-t-butylhydroquinone, 15.3 parts of diethyl 1-2-ethoxycarbonyl-5-methyl-hex-4-phosphonate, and 5.0 parts of Fulmont 237 are stirred at 130° C. for 24 hours. The cooled reaction is diluted with ether, washed with 10% sodium hydroxide solution and then with water. After stripping off the ether, the residual oil is distilled and gives a fraction $b_{0.4}$ 89°–156° C. and a residue. This residue is chromatographed on a column established from 150 parts silica, and an initial solvent mixture comprising petroleum-ether (b.p. 40°–60° C.) and 5% ethylacetate. Column elution is carried out by increasing the percentage of ether, and ultimately with 50% ether present, diethyl 5-(4-t-butyl-2,5-dihydroxyphenyl)-2-ethoxycarbonyl-5-methyl-hexane-2-phosphonate (formula (136)] is obtained as a viscous oil with the following percentage composition by weight.

|  | Carbon | Hydrogen | Phosphorus |
|---|---|---|---|
| Found | 61.16 | 8.52 | 6.61 |

|  | Carbon | Hydrogen | Phosphorus |
|---|---|---|---|
| Calculated for $C_{24}H_{41}O_7P$ | 60.99 | 8.74 | 6.55. |

EXAMPLE 16

2.2 Parts of hydroquinone, 8,5 parts of n-butyl citronellyl ether, and 0.5 parts of p-toluene sulphonic acid are heated on a steam-bath for 3 days. The work up follows Example 10 and, by short path distillation at 0.5 mb, there is obtained 2,5-bis-(8-n-butoxy-2,6-dimethyl-oct-2-yl)-hydroquinone [formula (137)] with m.p. 86°-89° C. and the following percentage composition by weight.

|  | Carbon | Hydrogen |
|---|---|---|
| Found | 76.43 | 11.88 |
| Calculated for $C_{34}H_{62}O_4$ | 76.35 | 11.68. |

EXAMPLE 17

Similarly obtained by the procedure of Example 16, using 6.2 parts of citronellol in place of the n-butylcitronellyl ether is obtained 2,5-bis-(2,6-dimethyl-8-hydroxy-oct-2-yl)-hydroquinone [formula (138)] as a viscous oil with the following percentage composition by weight

|  | Carbon | Hydrogen |
|---|---|---|
| Found | 74.18 | 11.07 |
| Calculated for $C_{26}H_{46}O_4$ | 73.89 | 10.97. |

EXAMPLE 18

By the procedure of Example 2, 4.8 parts of 2,5-bis (5-carboxy-2-methyl-pent-2-yl)-hydroquinone, 50 parts of tetrahydropyran-2-methanol, and 1.0 parts of p-toluene sulphonic acid are used to prepare 2,5-bis-(5-tetrahydropyran-4-yloxycarbonyl-2-methyl-pent-2-yl)-hydroquinone [formula (139)] with m.p. 155°-158° C. and the following percentage composition by weight.

|  | Carbon | Hydrogen |
|---|---|---|
| Found | 68.62 | 9.05 |
| Calculated | 68.30 | 8.90. |

EXAMPLE 19

5.0 Parts of 2,5-bis-(5-carboxy-2-methyl-pent-2-yl)-hydroquinone, 50 parts of commercial iso-octanol (mixed isomers, supplied by ICI Ltd.) and 1.0 parts of p-toluene sulphonic acid are reacted and worked up according to the procedure of Example 2. Short-path distillation at 0.5 mb using an oven temperature of 240° C. gave 2,5-bis-(2-methyl-5-iso-octyloxycarbonyl-pent-2-yl)-hydroquinone [formula (140)] as a viscous oil with the following percentage composition by weight.

|  | Carbon | Hydrogen |
|---|---|---|
| Found | 73.94 | 10.87 |
| Calculated for $C_{36}H_{62}O_6$ | 73.18 | 10.58. |

EXAMPLE 20

1.1 Parts of hydroquinone, 4.5 parts of ethyl 2-ethoxycarbonyl-5-methyl-hex-4-enoate, and 0.5 parts of p-toluene sulphonic acid, are heated on a steam-bath for 3 days. The reaction mixture is then diluted with ether, washed with 10% sodium hydroxide solution, water and evaporated. Short-path rotary distillation at 0.7 mb removed lower-boilers at an oven temperature of 120° C. The residue is crystallised from petroleum-ether (b.p. 40°-60° C.) containing 5% ethyl acetate and gives 2,5-bis-(5,5-diethoxycarbonyl-2-methyl-pent-2-yl)-hydroquinone [formula (141)] with m.p. 157°-160° C. and the following percentage composition by weight.

|  | Carbon | Hydrogen |
|---|---|---|
| Found | 63.90 | 8.28 |
| Calculated for $C_{30}H_{45}O_{10}$ | 63.59 | 8.18. |

EXAMPLE 21

83 Parts of 2-t-butylhydroquinone, 17.8 parts of dimethylphenylphosphonate, and 5.0 parts of Fulmont 237 (trademark) are stirred at 130° C. for 24 hours. The cooled reaction mixture is diluted with ether, filtered free of catalyst, and the ether solution washed firstly with 10% sodium hydroxide solution to remove t-butyl hydroquinone and then with water.

The ethereal extract is then evaporated and the residue diluted with 40°-60° petroleum ether containing ether. After being set aside at 0° C. there is obtained a light brown solid, m.p. 153°-165° C., which following a further crystallisation from ether containing a little acetone, gives dimethyl 3-(4-t-butyl-2,5-dihydroxyphenyl)-3-methyl-butane-phosphonate [formula (142)] with m.p. 193°-195° C. with the following percentage composition by weight.

|  | Carbon | Hydrogen | Phosphorus |
|---|---|---|---|
| Found | 59.99 | 8.38 | 8.62 |
| Calculated for $C_{17}H_{29}O_5P$ | 59.29 | 8.49 | 8.99. |

USE EXAMPLES

EXAMPLE 22

0.05 mMol of the magenta coupler of the formula

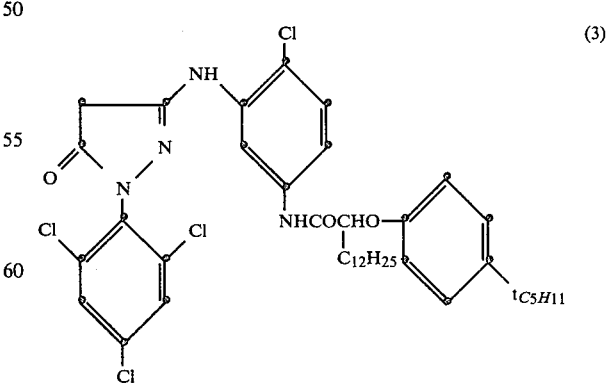

(3)

and 0.025 mMol of the hydroquinone compound of the formula (1) are dissolved in 2.0 ml of tricresylphosphate/ethyl acetate (0.75 g/100 ml). 7.0 ml of a 6% gelatin solution, 1.0 ml of a 0.8% solution of the wetting agent of the formula

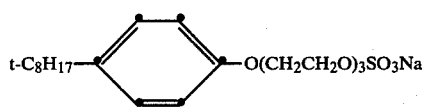

are put into water, then emulsified for 5 minutes by means of a 100-Watt ultra-sonic appliance. 2.5 ml of coupler-additive emulsion, freshly treated in the ultrasonic appliance, 2.0 ml of silver bromide emulsion with a content of 0.6% silver, 0.7 ml of a 1% aqueous solution of the curing agent with the following formula

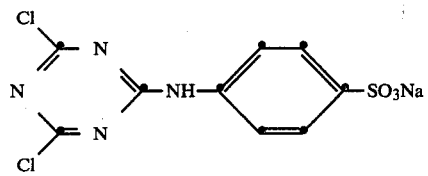

and 2.8 ml of water are mixed together, set to a pH value of 6.5, and at 40° C. poured onto a polyethylene paper measuring 14×18 cm. After the coating has hardened at 10° C., the poured-on mixture is dried at room-temperature.

Processing

The samples of the coated paper obtained are exposed to light of 500 Lux under a step-wedge for 6 seconds and then processed as follows at 32.8° C. (±0.3° C.):

| 1. Developer bath | 3.5 minutes |
|---|---|
| 2. Bleaching fixing bath | 1.5 minutes |
| 3. Washing | 3.0 minutes |
| 4. Drying | 1.0 minutes |

The developer bath has the following composition:

| 4-Amino-3-methyl-N—ethyl-N—[β-(methyl-sulphonamido)-ethyl]-aniline | 4.85 (g/liter) |
|---|---|
| 1½ H$_2$SO$_4$.H$_2$O | |
| Potassium bromide | 0.6 |
| Potassium carbonate | 32.0 |
| Lithium sulphate | 1.8 |
| Potassium sulphite | 2.0 |
| Hydroxylaminesulphite | 3.9 |
| Ethyleneglycol | 21.3 |
| Benzyl alcohol | 15.1 |
| Water | to 1 liter |
| The pH value is 10.1 | |

The bleaching fixing bath used is a conventional bath, with e.g. the following composition:

| Ammoniumthiosulphate (80% solution) | 200 (g/liter) |
|---|---|
| Sodium sulphite (anhydrous) | 15 |
| Sodium carbonate (anhydrous) | 2.5 |
| Ethylenediamine tetra-acetic acid, | 2 |
| Ethylenediamine tetra-acetic acid, sodium salt sodium-iron-(III)-salt | 50 |
| water | to 1 liter |

After washing and drying, clear, sharp magenta wedges are obtained with absorption maximum at 537 nm and maximum densities of 2.28.

A step-wedge obtained in this way is exposed to light in the Atlas apparatus (2500-W lamp) with 42 kJ/cm$^2$ through an ultraviolet filter (Kodak filter 2C). For comparison, a step-wedge which contains no compound according to the invention is prepared analogously.

In all cases the residual optical density (OD) is measured in % of the initial density (initial density 1). Table 2 contains the results.

TABLE 2

| Hydroquinone | % OD (with UV filter; 42 kJ/cm$^2$) |
|---|---|
| Without light stabilizer | 37 (control) |
| (104) | 80 |
| (105) | 84 |
| (106) | 87 |
| (108) | 85 |
| (110) | 78 |
| (131) | 76 |

If a hydroquinone compound of the formula

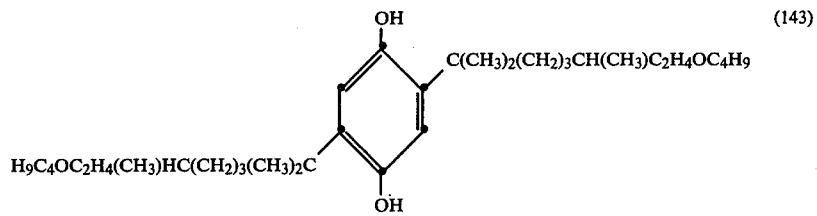

is incorporated into the above described emulsion and the resulting material is exposed, processed and exposed in the Atlas apparatus as shown, an OD-value of 90% is determined.

Compared with the emulsion without stabilizer, emulsions containing the above hydroquinone compounds are more stable to light.

EXAMPLE 23

In an analogous series of experiments to those described in Example 13, further compounds of the formula (1) are evaluated and the results are listed in Table 3.

TABLE 3

| Hydroquinone | % OD (with UV filter; 42 kJ/cm$^2$) |
|---|---|
| Without light stabilizer | 41 (control) |
| (109) | 88 |
| (111) | 85 |
| (125) | 87 |
| (126) | 91 |
| (127) | 78 |
| (123) | 58 |
| (130) | 55 |

Compared with the emulsion without stabilizer, emulsions containing the above hydroquinone compounds are more stable to light.

EXAMPLE 24

Emulsions prepared according to Example 21 containing compounds of the formula (1) are processed analogously and exposed to 42 kJ/cm² of light in the Atlas apparatus.

The increase in density measured at a wavelength of 436 (yellowing) is measured. The following values are obtained.

TABLE 4

| Hydroquinone | Increase 100 $D_{436}$ after 42 kJ/cm² in the Atlas Apparatus |
|---|---|
| Without light stabilizer | 11 (control) |
| (105) | 1 |
| (107) | 1 |
| (108) | 2 |
| (112) | 2 |

Compared with the emulsion without stabilizer, emulsions containing the above hydroquinone compounds show almost no increase in density 436.

EXAMPLE 25

Further samples are prepared according to Examples 21 and exposed over 52 days with 21 kJ/cm² behind a UV filter (Kodak Wratten 2C) at 40° C. and 30 to 40% relative humidity to fluoresence light. (Atlas Northlight fluorescence tubes, 40 W). The residual optical densities are measured in % of the initial density. These values are given in Table 5.

TABLE 5

| Hydroquinone | % OD (with UV filter, 21 kJ/cm²) |
|---|---|
| Without light stabilizer | 25 (control) |
| (104) | 94 |
| (110) | 91 |
| (106) | 94 |

EXAMPLE 26

Emulsions prepared according to Example 21 but containing 0.05 mMol of the magenta coupler of the following formula

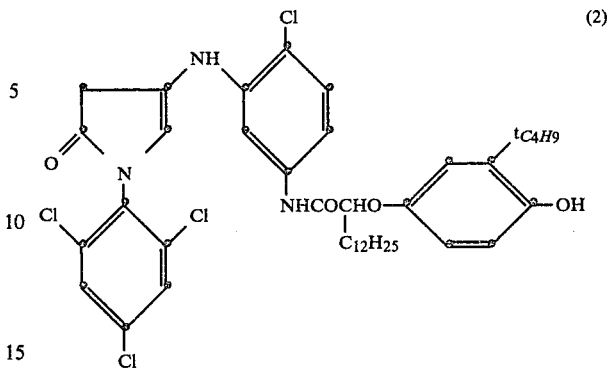

containing 0.025 mMol of the compound according to Example 9 is processed analogously and exposed to 42 kJ/cm² of light in the Atlas apparatus. The increase in density measured at a wavelength of 436 (yellowing) is measured. The following values are obtained.

TABLE 6

| Hydroquinone | Increase 100 $D_{436}$ after 42 kJ/cm² in the Atlas apparatus |
|---|---|
| Without light stabilizer | 10 |
| (104) | −1 |

Compared with the emulsion without stabilizer, emulsions containing the above hydroquinone compound show no increase in the D 436.-value.

The hydroquinone compounds of the formula (1), when incorporated into a silver halide emulsion according to Example 21 can be used in amounts of from 0.010 mMol to 0.1 mMol, preferably from 0.02 mMol to 0.05 mMol.

EXAMPLE 27

0.21 mMol of the azo dye of the formula

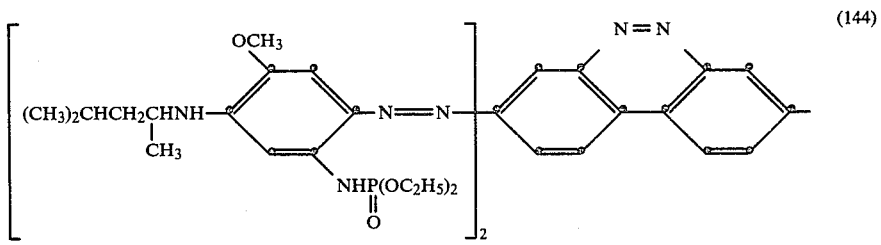

and 0.21 mMol of the hydroquinone of the formula (104) are mixed with 2.1 g of tricresylphosphate. Ethylacetate is added until a clear solution is obtained. 4.2 g of gelatin (as a 6% aqueous solution) and 2.5 ml of a 8% aqueous solution of the wetting agent are added. The mixture thus obtained is emulsified for 5 minutes by means of a 100 W ultrasonic appliance. To this emulsion a silver bromide emulsion is added which contains 4.3 g of gelatin and 1 g silver. Further, 10 ml of a 1% aqueous solution of a gelatin hardener are added. The final coating solution is adjusted to a pH-value of 6.5 and coated onto a support to give 1 m² of a photographic material.

An identical material is prepared which contains, however, no hydroquinone compound. This material is used as control.

Both materials are exposed to light under a step-wedge (100 lux, 2 seconds) and processed as follows at 30° C.:

| | | |
|---|---|---|
| (1) | developing | 3 minutes |
| (2) | washing | 1 minute |
| (3) | dye and silver bleaching | 5 minutes |
| (4) | washing | 1 minute |
| (5) | fixing | 4 minutes |
| (6) | washing | 6 minutes |
| (7) | drying. | |

The developer and fixing baths are of the usual composition as known in silver dye-bleach and black and white photography.

The combined dye and silver bleach bath contains per liter:

| | |
|---|---|
| sulfuric acid | 28 ml |
| m-nitrosulfonic acid (sodium salt) | 10 g |
| potassium iodide | 6 g |
| bis-(2-cyanoethyl)-(2-sulphoethyl)-phosphin (sodium salt) | 3 g |
| 2,3-dimethylquinoxalin | 1,5 g |

After processing the materials yield a clear and sharp magenta wedge with an absorption maximum at 540 nm. The processed materials are exposed to light as described in Example 21. Then the optical density before and after exposure is determined at the same point of the step wedge.

TABLE 7

| | OD | | loss of OD |
|---|---|---|---|
| Hydroquinone | before exp. | after exp. | in % |
| (104) | 1.37 | 1.12 | 18.3 |
| (control) | 1.25 | 0.69 | 44.8 |

This result shows that the hydroquinone of the formula (104) is an efficient stabiliser for azo image dyes.

EXAMPLE 28

The material accoding to Example 26 is used except that instead of the hydroquinone (104) 104 mg of the hydroquinone of the formula

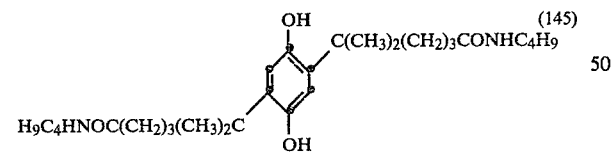

are incorporated. This material is exposed, processed and again exposed as described in Example 26. The OD-values determined are given in Table 8.

TABLE 8

| | OD | | loss of OD |
|---|---|---|---|
| Hydroquinone | before exp. | after exp. | in % |
| (145) | 1.0 | 0.65 | 35 |
| (control) | 1.0 | 0.48 | 52 |

It is evident that the incorporation of the hydroquinone of the formula (145) into colour photographic materials leads to an improved stability to light of this material.

I claim:

1. A colour photographic silver halide material which comprises on a support at least one colour coupler-containing silver halide emulsion layer, there being present in the silver halide emulsion layer(s) or in a layer adjacent to the silver halide emulsion layer(s)

(a) a hydroquinone compound of the formula

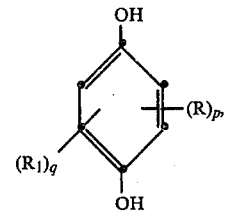

wherein p is 1 or 2 and q is 0 or 1, provided that p+q is 1 or 2, R is a radical of the formula

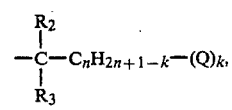

wherein Q is selected from the residues (1) —$COZR_4$, wherein Z is 0 or $NR_5$, and $R_4$ is hydrogen, alkyl having 1 to 20 carbon atoms, optionally interrupted by 1 to 5 oxygen atoms, and optionally substituted by a group $OR_6$, wherein $R_6$ is cycloalkyl having 3 to 12 carbon atoms, alkenyl having 3 to 20 carbon atoms, aryl having 6 to 10 carbon atoms optionally substituted by one or two alkyl groups (each) having 1 to 4 carbon atoms or aralkyl having 7 to 13 carbon atoms or $R_4$ is alkenyl having 3 to 20 carbon atoms or cycloalkyl having from 3 to 12 carbon atoms, aryl having from 6 to 10 carbon atoms optionally substituted by alkyl having 1 to 4 carbon atoms, or aralkyl having from 7 to 13 carbon atoms, a 5 or 6 membered heterocyclic ring containing an oxygen atom, and optionally substituted by one or two alkyl groups (each) having 1 to 4 carbon atoms, or methyl substituted by a 5- or 6-membered heterocyclic ring containing an oxygen atom and optionally substituted by one or two alkyl groups (each) having 1 to 4 carbon atoms, and when Z is —$NR_5$, $R_5$ is hydrogen or alkyl having 1 to 20 carbon atoms, or $R_4$ and $R_5$ together with the nitrogen atom to which they are bonded form a 5 or 6 membered heterocyclic ring, optionally substituted by one or two alkyl groups (each) having 1 to 4 carbon atoms;

(2) —OX, wherein X is $R_5$ or $COR_7$, wherein $R_5$ is as defined above and $R_7$ is hydrogen or alkyl having 1 to 20 carbon atoms, alkenyl having 3 to 20 carbon atoms, cycloalkyl having 3 to 12 carbon atoms, aralkyl having 7 to 13 carbon atoms or aryl having 6 to 10 carbon atoms, optionally substituted by one or two alkyl groups each having 1 to 4 carbon atoms;

(3) —$NR_8R_9$ wherein $R_8$ is hydrogen or alkyl having 1 to 4 carbon atoms and $R_9$ is hydrogen, alkyl having 1 to 4 carbon atoms or —$COR_7$, wherein $R_7$ is as defined above, or $R_8$ and $R_9$, together with the nitrogen atom to which they are bonded, form a 5- or 6-membered ring, optionally substituted by one or two alkyl groups (each) having 1 to 4 carbon atoms;

(4) —P(O)(OR$_{10}'$)([O]$_x$R$_{11}'$) wherein x is 0 or 1, and if x is 1, R$_{10}'$ and R$_{11}'$ are independently of each other hydrogen or alkyl having 1 to 20 carbon atoms or R$_{10}'$ and R$_{11}'$ are linked together to form an alkylene chain having 2 or 3 carbon atoms optionally substituted by one or more alkyl groups each having 1 to 20 carbon atoms, and if x is 0, R$_{10}'$ is alkyl having 1 to 5 carbon atoms;

(5) —SO$_2$R$_{12}'$, wherein R$_{12}'$ is hydroxyl, chlorine or —NR$_5$R$_7$, wherein R$_5$ and R$_7$ are as defined above, provided that, if R$_{12}'$ is hydroxyl, R$_1$ is a residue of formula

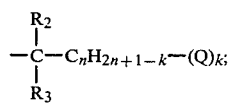

or (6) cyano;

n is an integer from 1 to 20, k is 1 or 2,

R$_2$ and R$_3$ are independently of each other alkyl having 1 to 5 carbon atoms and, if Q is CO$_2$R$_4$, either R$_2$ or R$_3$ is optionally substituted by —CO$_2$R$_4$, or R$_2$ or R$_3$ is so linked to the residue C$_n$H$_{2n+1-k}$ that there is formed a cycloalkylene residue having 5 to 12 carbon atoms substituted by —(CO$_2$R$_4$)$_k$, wherein R$_4$ and k are as defined above, R$_1$ is alkyl having 1 to 8 carbon atoms, or a residue of formula

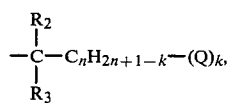

and if R$_1$ is a residue of this formula, then R$_1$ and R are the same or different; or (b) there being present salts thereof with organic or inorganic acids or bases.

2. A material according to claim 1, wherein the hydroquinone corresponds to the formula

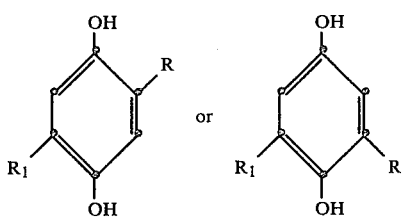

wherein R and R$_1$ are as defined in claim 1, or to salts thereof with organic or inorganic acids or bases.

3. A material according to claim 1, wherein the hydroquinone corresponds to the formula

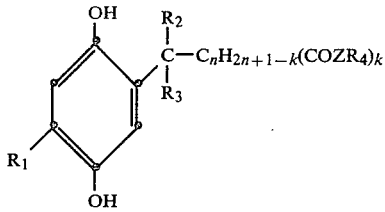

or

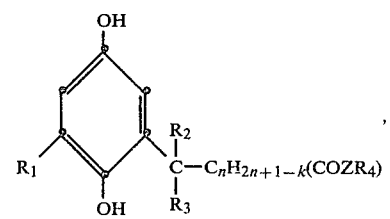

wherein

Z is O or NR$_5$ and

R$_4$ is hydrogen, alkyl having from 1 to 20 carbon atoms optionally interrupted by 1 to 5 oxygen atoms and optionally substituted by —OR$_6$, wherein R$_6$ is cycloalkyl having 3 to 12 carbon atoms, alkenyl having 3 to 20 carbon atoms, aryl having 6 to 10 carbon atoms optionally substituted by one or two alkyl groups (each) having 1 to 4 carbon atoms, or aralkyl having 7 to 13 carbon atoms, or R$_4$ is alkenyl having 3 to 20 carbon atoms, aryl having 6 to 10 carbon atoms optionally substituted by alkyl having 1 to 4 carbon atoms, cycloalkyl having 3 to 12 carbon atoms, aralkyl having 7 to 13 carbon atoms, a 5 or 6 membered heterocyclic ring containing an oxygen atom which ring is optionally substituted by one or two alkyl groups (each) having 1 to 4 carbon atoms or R$_4$ is methyl substituted by a 5 or 6 membered heterocyclic ring containing an oxygen atom which ring is optionally substituted by one or two alkyl groups (each) having 1 to 4 carbon atoms, R$_5$ is hydrogen or alkyl having 1 to 20 carbon atoms or R$_4$ and R$_5$ together with the nitrogen atom to which they are bonded form a 5 or 6 membered heterocyclic ring optionally substituted by one or two alkyl groups (each) having 1 to 4 carbon atoms, k is 1 or 2 and n is an integer from 1 to 20, R$_2$ and R$_3$, independently of each other, are alkyl each having 1 to 5 carbon atoms and either R$_2$ or R$_3$ is optionally substituted by —COZR$_4$, wherein Z and R$_4$ are as defined above, or R$_2$ or R$_3$ are so linked to the residue C$_n$H$_{2n+1-k}$ that there is formed a cycloalkylene residue having 5 to 12 carbon atoms which is substituted by (COZR$_4$)$_k$ wherein k, Z and R$_4$ are as defined above, and R$_1$ is a group of the formula

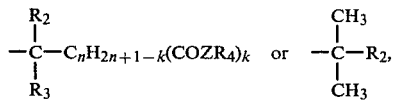

wherein R$_2$, R$_3$, R$_4$, k, Z and n are as defined above, or to salts thereof with organic or inorganic acids or bases.

4. A photographic material according to claim 3, wherein the hydroquinone corresponds to the formula

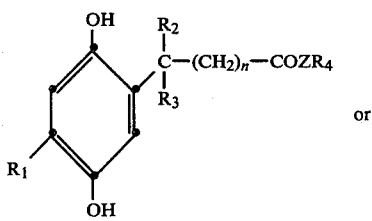

or

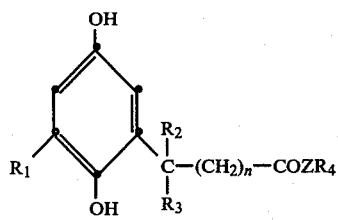

wherein

R$_4$, Z and n are as defined in claim 3,

R$_2$ and R$_3$, independently of each other, are alkyl each having 1 to 5 carbon atoms and either R$_2$ or R$_3$ is optionally substituted by —COZR$_4$, wherein Z and R$_4$ are as defined above, or R$_2$ or R$_3$ may be so linked to the residue C$_n$H$_{2n}$ that there is formed a cycloalkylene residue having 5 to 12 carbon atoms which is substituted by —COZR$_4$, wherein R$_4$ and Z are as defined above, and R$_1$ is a group of the formula

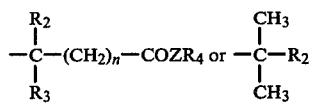

wherein R$_2$, R$_3$, R$_4$, Z and n are as defined above, or to salts thereof with organic or inorganic acids or bases.

5. A photographic material according to claim 4, wherein the hydroquinone corresponds to the formula

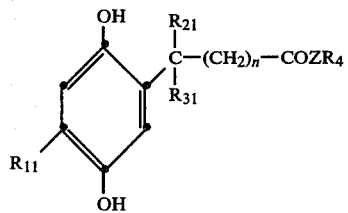

wherein

R$_{21}$ and R$_{31}$, independently of each other, are methyl, ethyl, n-propyl, i-propyl or neopentyl and either R$_{21}$ or R$_{31}$ is optionally substituted by —COZR$_4$, wherein R$_4$ and Z are as defined in claim 4, or R$_{21}$ or R$_{31}$ are so linked to the residue (CH$_2$)$_n$ that there is formed a cycloalkylene residue having 5 to 8 carbon atoms which is optionally substituted by COZR, wherein R$_4$ and Z are as defined above, R$_{11}$ is a group of the formula

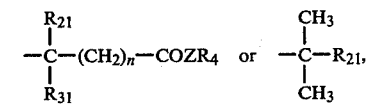

wherein

R$_{21}$, R$_{31}$, R$_4$ and Z are as defined above and n is as defined in claim 4, or to salts thereof with organic or inorganic acids or bases.

6. A photographic material according to claim 5, wherein the hydroquinone compound corresponds to the formula

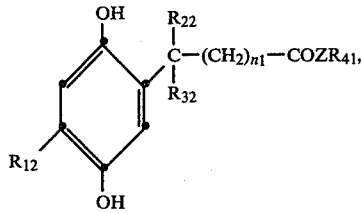

wherein

R$_{41}$ is hydrogen, alkyl having from 1 to 20 carbon atoms optionally interrupted by 1, 2 or 3 oxygen atoms and optionally substituted by —OR$_{61}$ wherein R$_{61}$ is cyclopentyl, cyclohexyl or cyclooctyl, alkenyl having 3 to 10 carbon atoms, phenyl or naphthyl optionally substituted by 1 or 2 alkyl groups (each) having 1 to 4 carbon atoms, benzyl, phenylethyl, benzhydryl or naphthylmethyl, or R$_{41}$ is alkenyl having 3 to 15 carbon atoms, phenyl or naphthyl optionally substituted by 1 or 2 alkyl groups (each) having 1 to 4 carbon atoms, cyclopentyl, cyclohexyl, cyclooctyl, benzyl, phenylethyl, benzhydryl or naphthylmethyl, or R$_{41}$ is a 5 or 6 membered heterocyclic ring containing an oxygen atom which ring is optionally substituted by 1 or 2 alkyl groups (each) having 1 to 4 carbon atoms or R$_{41}$ is methyl substituted by a 5 or 6 membered heterocyclic ring containing an oxygen atom which ring is optionally substituted by 1 or 2 alkyl groups (each) having 1 to 4 carbon atoms, R$_{22}$ and R$_{32}$ independently of each other, are methyl, ethyl or neopentyl cyclohexylene residue, which is optionally substituted by —COZR$_4$, wherein Z and R$_4$ are as defined in claim 5, R$_{12}$ is a group of the formula

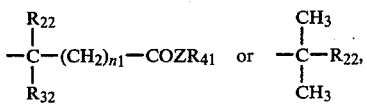

wherein

R$_{22}$, R$_{32}$ and R$_{41}$ are as defined above and n$_1$ is an integer from 1 to 10 and Z is as defined above, or to salts thereof with organic or inorganic acids or bases.

7. A photographic material according to claim 6, wherein the hydroquinone compound corresponds to the formula

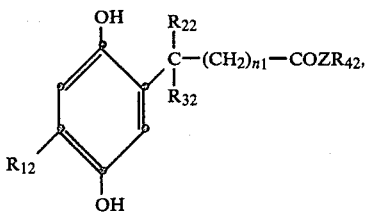

wherein

Z is O or $NR_{51}$ $R_{42}$ is alkyl having from 1 to 20 carbon atoms optionally interrupted by 1 or 2 oxygen atoms and optionally substituted by $-OR_{62}$, wherein $R_{62}$ is cyclohexyl, alkenyl having 3 to 10 carbon atoms, phenyl or benzyl, or $R_{42}$ is alkenyl having 3 to 15 carbon atoms, phenyl, benzyl, phenylethyl, cyclopentyl or cyclohexyl or $R_{42}$ is a 5 or 6 membered heterocyclic ring containing an oxygen atom or $R_{42}$ is methyl substituted by a 5 or 6 membered heterocyclic ring containing an oxygen atom, $R_{51}$ is hydrogen or alkyl having 1 to 15 carbon atoms, and $R_{12}$, $R_{22}$, $R_{32}$ and $n_1$ are as defined in claim 6, or to salts thereof with organic or inorganic acids or bases.

8. A photographic material according to claim 7, wherein the hydroquinone compound corresponds to the formula

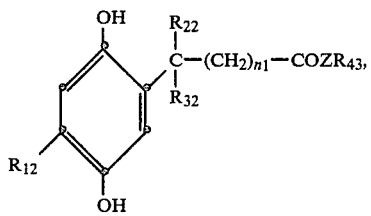

wherein $R_{43}$ is alkyl having 1 to 16 carbon atoms optionally interrupted by an oxygen atom and optionally substituted by phenoxy, or $R_{43}$ is alkenyl having 3 to 15 carbon atoms, phenyl, benzyl, tetrahydrofuran-3-yl, tetrahydropyran-4-yl or tetrahydrofurfuryl and Z, $R_{12}$, $R_{22}$, $R_{32}$, $R_{51}$ and $n_1$ are as defined in claim 7, or to salts thereof with organic or inorganic bases.

9. A photographic material according to claim 8, wherein a salt is present produced by reaction of the hydroquinones according to claim 8 with tetra-alkyl ammonium hydroxides or alkali or alkaline earth hydroxides or carbonates.

10. A photographic material according to claim 8, wherein the hydroquinone compound corresponds to the formula

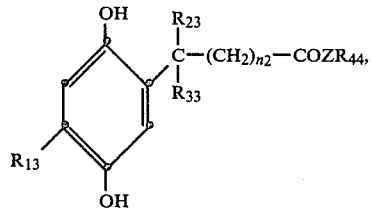

wherein $R_{44}$ is alkyl having 1 to 16 carbon atoms optionally interrupted by an oxygen atom and optionally substituted by phenoxy, or $R_{44}$ is phenyl, benzyl, tetrahydrofuran-3-yl, furfuryl or tetrahydrofurfuryl, and Z and $R_{51}$ are as defined in claim 8, $R_{23}$ and $R_{33}$, independently, are methyl or neopentyl, $R_{13}$ is a group of the formula

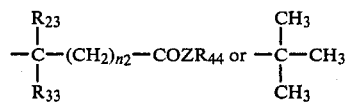

wherein $R_{23}$, $R_{33}$ and $R_{44}$ are as defined above, and $n_2$ is an integer from 1 to 3.

11. A photographic material according to claim 1, wherein the hydroquinone corresponds to the formula

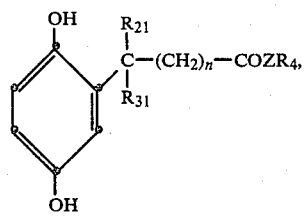

wherein n, Z, $R_4$, $R_{21}$ and $R_{31}$ are as defined in claim 5.

12. Photographic material according to claim 1, wherein the hydroquinone corresponds to the formula

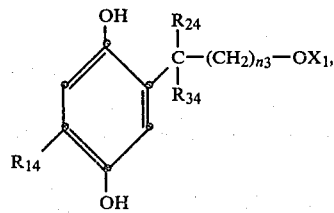

wherein $X_1$ is $COR_7$, wherein $R_7$ is hydrogen or alkyl having 1 to 10 carbon atoms, or $X_1$ is hydrogen or alkyl having 1 to 10 carbon atoms, $R_{24}$ and $R_{34}$ are independently of each other methyl or ethyl, and $R_{14}$ is a group of the formula

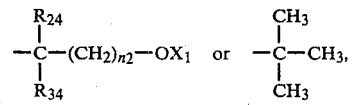

wherein $X_1$, $R_{24}$ and $R_4$ are as defined above and $n_3$ is an integer from 1 to 6.

13. Photographic material according to claim 1, wherein the hydroquinone corresponds to the formula

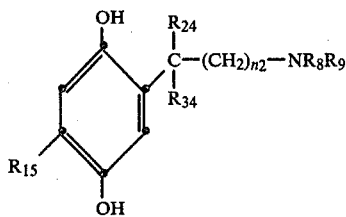

wherein
$R_8$ is hydrogen, methyl or ethyl, $R_9$ is hydrogen, methyl, ethyl or $COR_7$, wherein $R_7$ is as defined in claim 12,
$R_{15}$ is a group of the formula

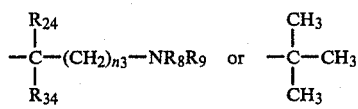

wherein $R_8$ and $R_9$ are as defined above and $R_{24}$, $R_{34}$ and $n_3$ are as defined in claim 12.

14. Photographic material according to claim 1, wherein the hydroquinone corresponds to the formula

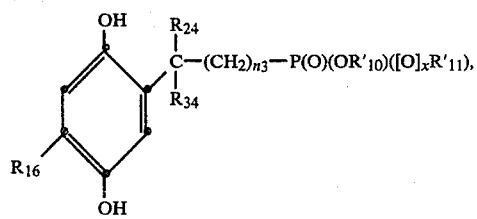

wherein
x is 1 or 0, $R_{10}'$ and $R_{11}'$ are independently of each other hydrogen or alkyl having 1 to 12 carbon atoms if x is 1, and are alkyl having 1 to 5 carbon atoms if x is 0,
$R_{16}$ is a group of the formula

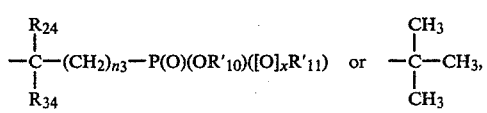

wherein x, $R_{10}'$ and $R_{11}'$ are as defined above, and $R_{24}$, $R_{34}$ and $n_3$ are as defined in claim 12.

15. Photographic material according to claim 1, wherein the hydroquinone corresponds to the formula

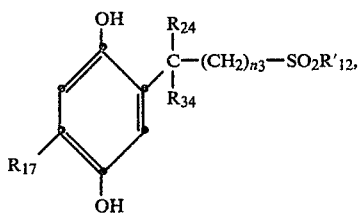

wherein
$R_{12}'$ is hydroxyl, chlorine or amino optionally substituted by alkyl having 1 to 10 carbon atoms,
$R_{17}$ is a group of the formula

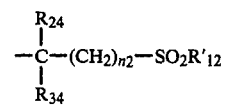

wherein
$R_{12}'$ is as defined above,
$n_3$, $R_{24}$ and $R_{34}$ are as defined in claim 12.

16. Photographic material according to claim 1, wherein the hydroquinone corresponds to the formula

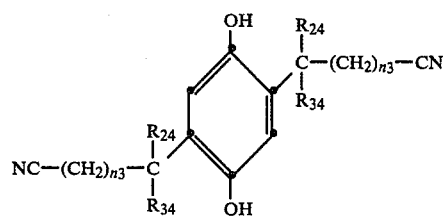

wherein $R_{24}$, $R_{34}$ and $n_3$ are as defined above.

17. A photographic material according to claim 1, wherein the hydroquinone corresponds to the formula

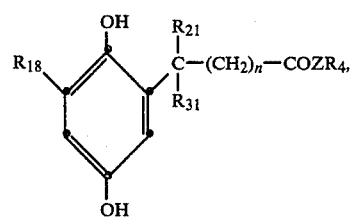

wherein $R_{21}$, $R_{31}$, $R_4$, Z and n are as defined in claim 5, and $R_{18}$ is a group of the formula

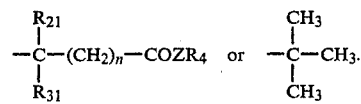

18. A photographic material according to claim 1, wherein the colour coupler is a magenta coupler.

19. A photographic material according to claim 18, wherein the magenta coupler has the formula

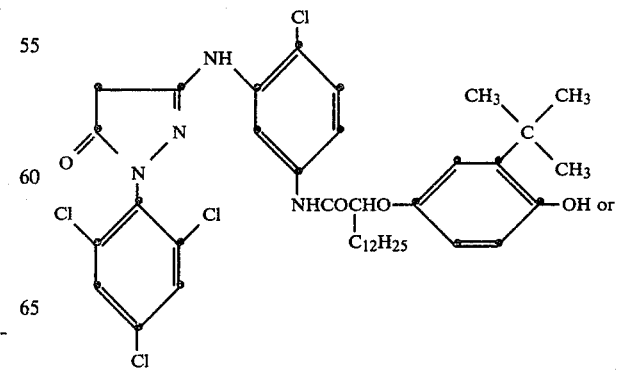

-continued

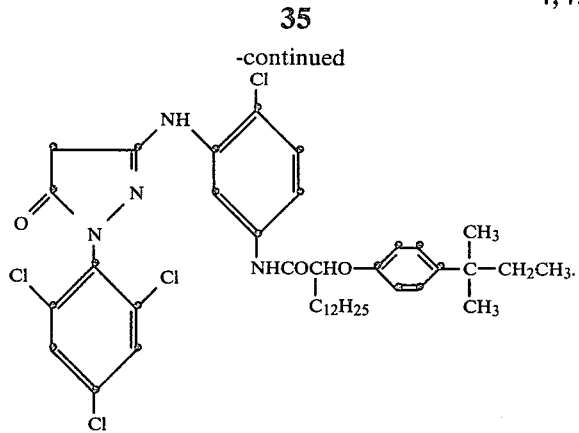

20. A method for the preparation of a silver halide material according to claim 1, wherein a hydroquinone according to claim 1 is incorporated into at least one silver halide emulsion layer containing a colour coupler or into a layer adjacent to the silver halide emulsion layer.

21. A method for the preparation of a silver halide material according to claim 3, wherein a hydroquinone according to claim 3 is incorporated into at least one silver halide emulsion layer containing a colour coupler or into a layer adjacent to the silver halide emulsion layer.

* * * * *